(12) United States Patent
Ruddle et al.

(10) Patent No.: US 7,261,561 B2
(45) Date of Patent: Aug. 28, 2007

(54) VIBRATIONAL DRIVER FOR ENDODONTIC ACTIVATORS

(76) Inventors: Clifford J. Ruddle, 227 Las Alturas Rd., Santa Barbara, CA (US) 93103; Robert H. Sharp, 2 Scripps Dr., Ste. 210, Sacramento, CA (US) 95825

( * ) Notice: Subject to any disclaimer, the term of this patent is extended or adjusted under 35 U.S.C. 154(b) by 172 days.

(21) Appl. No.: 11/182,093

(22) Filed: Jul. 15, 2005

(65) Prior Publication Data

US 2007/0015108 A1    Jan. 18, 2007

(51) Int. Cl.
*A61C 3/03* (2006.01)
(52) U.S. Cl. .................................. 433/122; 433/224
(58) Field of Classification Search ............... 433/102, 433/118–119, 122–124, 224
See application file for complete search history.

(56) References Cited

U.S. PATENT DOCUMENTS

| | | | |
|---|---|---|---|
| 3,073,031 A | | 1/1963 | Brenman et al. |
| 3,829,974 A | * | 8/1974 | McShirley .................. 433/124 |
| 4,460,341 A | * | 7/1984 | Nakanishi .................. 433/122 |
| 4,629,426 A | * | 12/1986 | Levy .......................... 433/118 |
| 4,773,855 A | * | 9/1988 | Levy .......................... 433/102 |
| 5,169,312 A | * | 12/1992 | Berlin ........................ 433/123 |
| 5,343,883 A | | 9/1994 | Murayama |
| 5,636,988 A | | 6/1997 | Murayama |
| 5,827,064 A | * | 10/1998 | Bock .......................... 433/216 |
| 5,855,216 A | * | 1/1999 | Robinson .................... 132/322 |
| 5,902,105 A | * | 5/1999 | Uejima et al. .............. 433/27 |
| 5,924,864 A | * | 7/1999 | Loge et al. .................. 433/118 |
| 6,447,293 B1 | | 9/2002 | Sokol et al. |
| 6,760,945 B2 | | 7/2004 | Ferber et al. |
| 2001/0034006 A1 | * | 10/2001 | Lang et al. ................. 433/118 |
| 2003/0162146 A1 | * | 8/2003 | Shortt et al. ............... 433/118 |
| 2006/0068361 A1 | * | 3/2006 | Bergler et al. ............. 433/86 |

OTHER PUBLICATIONS

Oral-B Sonic Complete web page—May 4, 2005—2 pages.
European Search Report, corresponding to European application No. 06100089, dated Nov. 2, 2006.

* cited by examiner

*Primary Examiner*—Cris Rodriguez
*Assistant Examiner*—Sunil K. Singh
(74) *Attorney, Agent, or Firm*—Polster, Lieder, Woodruff & Lucchesi, L.C.

(57) ABSTRACT

A contra-angled driver receives an endodontic activator to induce vibrations and/or oscillations in the activator at sonic frequencies. The driver includes a quick connect/disconnect to allow for quick and simple mounting and dismounting of the activator.

13 Claims, 5 Drawing Sheets

VIBRATIONAL DRIVER FOR ENDODONTIC ACTIVATORS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

This invention relates to endodontic tools, and in particular, to a driver to vibrate an activator to enhance cleaning of root canals during an endodontic procedure.

Following tooth maturation, the dental pulp is harbored within the structural elements of the tooth. Frequently, and for a variety of reasons, the pulp is irreversibly injured, resulting in inflammatory and infectious conditions which often adversely affect the tooth and its supporting structures. Clinically, as an alternative to extraction, root canal treatment is performed and ideally directed towards the elimination of pulp, bacteria, and related irritants from the root canal system, followed by three-dimensionally filling the root canal space with an inert, biocompatible, dimensionally stable, filling material, such as gutta percha. Ideally, the obturation procedures will fill not just the main canal, but the fins, webs, cul-de-sacs, lateral canals, and all portals of exit between the root canal system and the tooth's attachment apparatus.

Central to a successful endodontic (or root canal) treatment has been the use of chemical reagents during mechanical root canal shaping procedures to completely clean all aspects of the root canal system. The chemicals used to enhance canal debridement and disinfection during cleaning and shaping procedures potentially reach all aspects of the root canal system. The most popular chemicals currently used during canal preparation to actively assist in cleaning and disinfecting include bleach, hydrogen peroxide, and chelating agents. Often, a 2%-5% solution of a clear, pale, greenish-yellow strongly alkaline solution of sodium hypochlorite (NaOCl) and ethylenediaminetetracetic acid (EDTA) are used.

During canal preparation, a solution of NaOCl is liberally irrigated into the root canal space where its solvent action facilitates the digestion and removal of pulp, bacteria, viruses, spores, endotoxins and other irritants generated by the microorganisms. This solution has the potential to circulate, penetrate and, hence, clean into all aspects of the root canal space. However, studies have shown that even the most thorough use of sodium hypochlorite does not remove all the material from the root canal. The walls of a root canal are comprised of dentin, which contains millions of dentinal tubules per square millimeter. Instruments used to negotiate and shape a canal cut dentin and dentin, in combination with organic substrates, forms dentinal mud. Dentinal mud, pulp, bacteria, and other related irritants have been consistently visualized histologically after cleaning and shaping procedures in the dentinal tubules and various aspects of the root canal systems. Thus, after cleaning and shaping procedures, the root canal is still covered with a film of debris, frequently described in the literature as a "smear layer." This "smear layer" includes dentinal mud and/or organic debris, including the irritants noted above.

After cleaning and shaping, the root canal has been traditionally filled with gutta percha and a root sealer. However, if the smear layer or film is not adequately removed from the root canal, the smear layer can compromise the filling and sealing of the root canal system. If obturation is incomplete then the root canal space is predisposed to bacterial leakage and failure. Post-treatment failures attributable to leakage are common and require endodontic retreatment of the tooth or extraction. Thus, for a complete and thorough cleaning, this smear layer or film should be removed. To address the smear layer, practitioners use a weak acid or surfactant, such as 17% EDTA, in an effort to remove the smear layer. Typically, the root canal is flushed with EDTA, or other final rinse solutions, to accomplish this. Traditionally, some practitioners have used a metal root canal file or a cannula to activate the solution and enhance the performance of the EDTA. These devices may be used manually or mounted in an ultrasonic handpiece to produce vibrations and fluid movement. As an example, even when a file is used, it is impossible to ensure that the file is brought into contact with the complete surface of the root canal, and hence it is difficult to ensure that substantially all of the smear layer has been removed. Regrettably, the use of ultrasonically driven metal instruments has frequently led to iatrogenic events, such as broken instruments, ledges in the wall of the root canal preparation, or even perforation of the root canal. Hence the use of such instruments is not desirable.

U.S. Pat. No. 6,179,617 and Published U.S. application Ser. No. 20040214135, both of which are incorporated herein by reference, disclose an endodontic brush for use in removing the smear layer. A brush can work well to remove the smear layer from the main path of the root canal. However, the brush bristles may not extend into the fins, webs, cul-de-sacs, anastomoses, lateral canals, and portals of exit between the root canal system and the tooth's attachment apparatus. Hence, while the brush may effectively remove the smear layer from the main canal, these fins, webs, lateral canals, etc. may still contain pulp, bacteria and related irritants, which may then compromise sealing the canal.

Currently, ultrasonically activated endodontic instruments, are used, at times, to enhance the cleaning of a shaped canal prior to three-dimensional filling. Such instruments include, for example, the BUC® tips sold by SybronEndo, the ProUltra™ tips sold by Dentsply, and the CPR® tips sold by Obtura. These metal instruments are connected to an ultrasonic driver. The tips generally are contra-angled tips. For the ultrasonic energy to efficiently pass through the contra-angled portion and along the overall length to the tip, the instrument is required to be securely connected to the driver. To this end, these instruments are all connected to the drive by threads which require a wrench to fully and securely connect the instruments to the drive. Multiple tips may be used in a single procedure. As can be appreciated, the need to use a wrench to connect a tip to the driver and to then disconnect the tip from the driver increases the time involved in mounting and dismounting of the tips. Because these instruments oftentimes have abrasive coatings and additionally cut toward their tips, they should not be used to remove the smear layer.

I have found that by vibrationally driving a non-cutting activator, the cleaning solution can be made turbulent, inducing cavitation at the end of the activator and acoustic streaming along the length of the activator, thereby enhancing the removal of the smear layer from both a shaped root canal, and importantly, from the fins, webs, lateral canals, etc. commonly comprising root canal system anatomy.

BRIEF SUMMARY OF THE INVENTION

Briefly stated, a driver is provided to induce vibration and drive an endodontic activator. In an illustrative embodiment, the driver comprises a body having a handle and a neck. As seen in the drawing figures, the driver body can have a contra-angle design. Illustratively, the driver is cordless and contains rechargeable batteries as a power source. The driver, however, could be corded, or be configured to accept non-rechargeable batteries.

A driven member is mounted in the body for pivotal motion about an axis. The driven member comprises a mounting ring, a mounting arm and a connecting arm. The housing comprises a pair of opposed arms at the end of the handle neck, and the arms define a gap. The driven member is mounted in the gap. A rod passes between the handle arms, and the driven member mounting ring is journaled on the rod. The mounting arm and connecting arm can define an angle of between about 80° and about 90°.

A driving means is mounted within the handle and is operatively connected to the driven member to induce vibratory and/or oscillatory motion in the driven member. In the illustrative embodiment, the driving means comprising a block which is rotated about an axis of rotation. The block defines a pocket on an end surface which receives the driven member connecting arm. The pocket is off-set from the axis of rotation so that rotation of the block member will create oscillatory motion in the driven member connecting arm, which is passed onto the driven member mounting arm, such that the driven member mounting arm will vibrate. The block can be rotated, for example, by a motor.

When activated, the driver induces vibrations/oscillations in a sonic frequency range (i.e., less than about 15 kHz). The driver includes a speed control to enable the oscillatory speed of the endodontic activating tip to be selectively changed and operate at different speeds or frequencies. The speed control can allow for the selection of a speed along a continuum of speeds between a high speed to a low speed. Alternatively, the speed control can have, for example, three set speeds (i.e., high, medium and low).

The endodontic activator includes a mounting block defining a pocket which is shaped complimentarily to an end of the driven member mounting arm and which is sized to be frictionally and removably received on the driven member mounting arm. An activating tip extends from the mounting block. The size and shape of the endodontic activator mounting block allows for the activator to be mounted to the driven member mounting arm (and hence to the driver) quickly, easily, and without the use of tools.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figure 1:
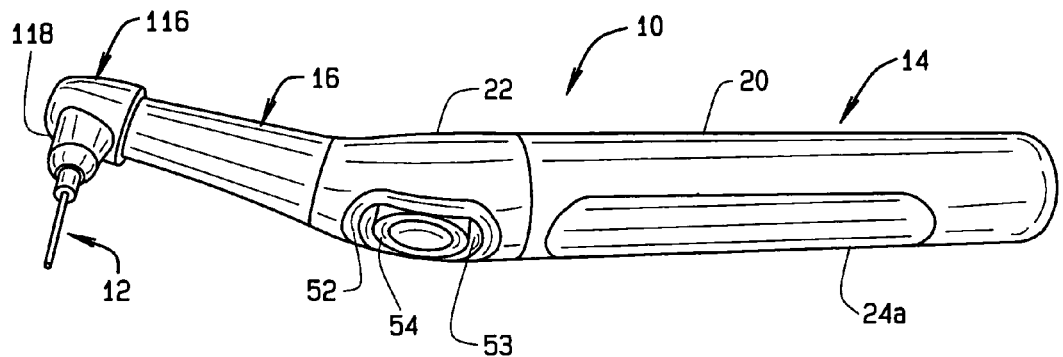
FIG. 1 is a bottom perspective view of an illustrative embodiment of a driver of the present invention.

The following detailed description illustrates the invention by way of example and not by way of limitation. This description will clearly enable one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Figure 2:
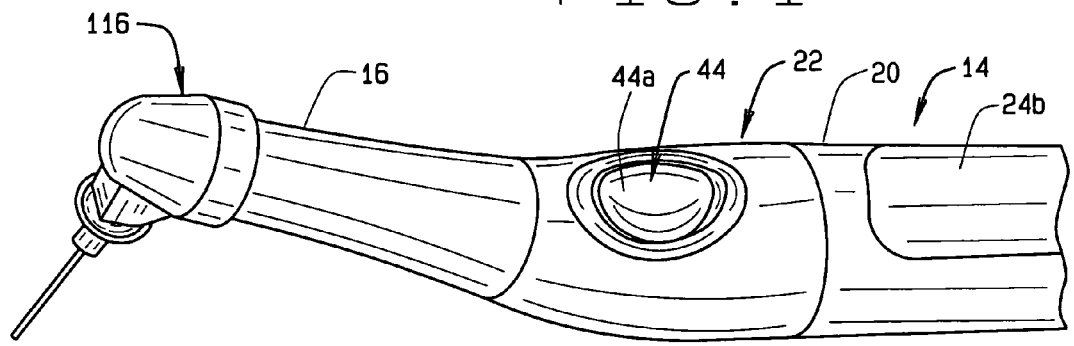
FIG. 2 is a top perspective fragmentary perspective view of the driver.
Figure 3:
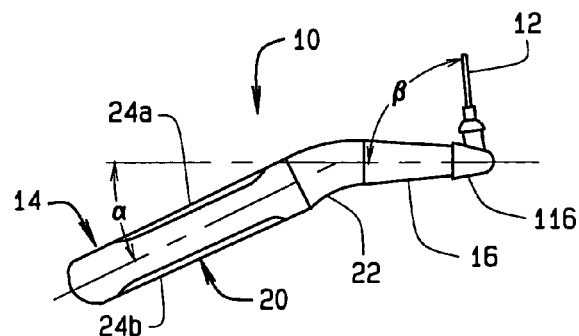
FIG. 3 is a side elevational view of the driver.
Figure 4:
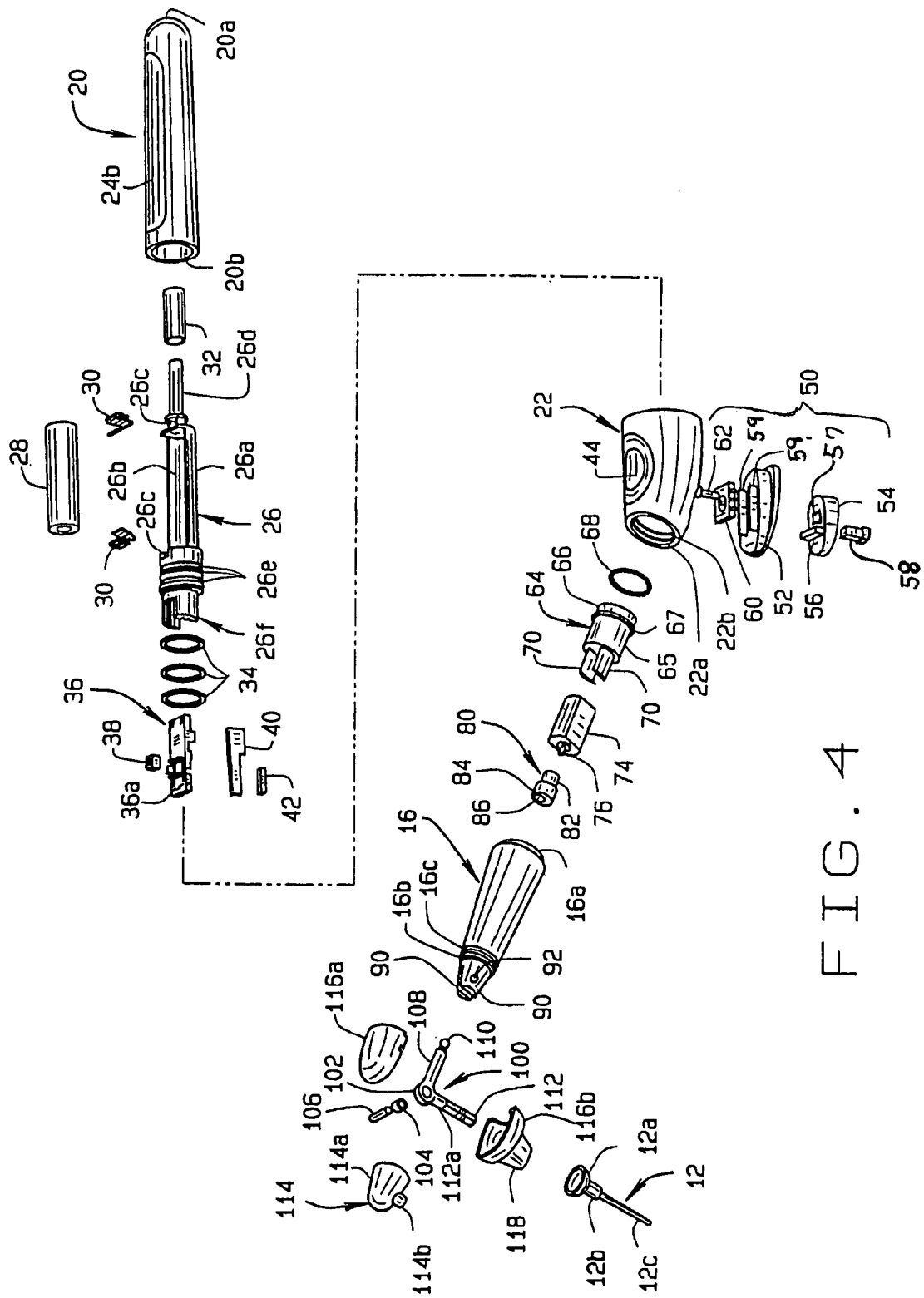
FIG. 4 is an exploded perspective view of the driver.

An illustrative embodiment of a driver 10 of the present invention for driving an endodontic activator 12 is shown generally in FIGS. 1-3. The activator 12 is preferably an activator such as is described in co-pending application Ser. No. 11/104,678, filed Apr. 13, 2005, entitled "Apparatus And Method For Preparing A Root Canal" and which is incorporated herein by reference. The activator 12 comprises a guard 12a, a connection block 12b defining a pocket, and a tip 12c (FIG. 4). The driver 10 comprises a handle 14 and a neck 16. The driver or handpiece 10 is a contra-angled handpiece, and hence the handle 14 and the neck 16 define an angle α (FIG. 3) of about 15° to about 30°, and preferably about 25°. The activator 12 is mounted to the driver, such that the activator forms an angle β of about 80° to about 85° with the axis of the neck 16.

The handle 14 and neck 16 are both hollow and in combination define a housing for the elements which drive the activator 12. The housing members 14 and 16 are made from an FDA approved plastic, such as ABS and/or polycarbonate. The housing members could be made from any other desired material.

The handle 14 is comprised of a body 20 and a forward section or connector 22. The handle body 20 is closed at its back end 20a and opened at its forward end 20b and defines a battery compartment. Externally, the handle body is provided with textured rubber grip areas 24a,b on opposite sides of the handle body. These grip areas can be co-molded with the handle body 20 and provide non-slip areas for a practitioner to grasp the driver 10.

A battery mount 26 is received in the battery compartment defined by the handle body 20. The battery mount 26 includes a main section 26a which forms a cradle 26b sized and shaped to receive a battery 28. Contacts 30 are mounted in pockets 26c located at opposite ends of the cradle 26b. A stem 26d extends from the bottom of the mount 26. A charging unit 32 can be placed about the stem 26d to allow for the use of rechargeable batteries. If a charging unit 32 is provided, the handle body 20 will be provided with appropriate means to allow for electrical connection of the body to a source of electricity to enable the battery 28 to be recharged. Such connection means can include external contacts, in which case the driver would be received in a charging base which, in turn, is connectable to a source of electricity. Alternatively, the connection means can comprise a socket which receives a connector end of a charging adapter having prongs enabling the adapter to be plugged directly into an electrical outlet. In either situation, such connection means are well known to those skilled in the art and are not described herein. Alternatively, handle body 20 can be configured to allow for replacement of the batteries. This would allow for replacement of rechargeable batteries or for the use of non-rechargeable batteries. As can be appreciated, the use of a battery operated driver enables the driver to be cordless. As another alternative, the driver could be configured to be a corded driver. In this case, an electrical cord would be provided. Such a cord could have a plug on its end for connection to a wall outlet or other electrical outlet. As a further alternative, an electrical cord could be hardwired to a control panel.

The forward end of the mount 26 is provided with circumferential grooves 26e which receive O-rings 34. The mount 26 and the O-rings 34 are sized such that the O-rings form a fluid-tight seal between the internal surface of the handle body 20 and the mount 26 at the forward end of the mount 26. When the mount 26 is received in the handle body 20, the O-rings 34 will be approximately flush with the opened end 20b of the handle body 20. A bracket 26f extends from the end of the mount 26 forwardly of the O-ring grooves 26e. When the mount 26 is received in the handle body 20, the bracket 26f will extend from the forward end 20b of the handle body 20.

A switch fixture 36 is received in the bracket 26f. The switch fixture 36 is generally rectangular in shape, having first and second sides. On one side, the switch fixture 36 includes two sets of opposed arms 36a which snappingly receive and hold a spring biased button 38. The button 38 is movable radially with respect to the handle (i.e., generally perpendicularly relative to the switch fixture 36). A control board 40 and a sliding switch 42 are received and supported on the opposite side of the switch fixture 36.

The switch fixture 36 and the associated button 38, control board 40 and switch 42 form a control assembly which is enclosed by the handle forward section 22. The handle forward section 22 includes a flexible membrane 44 (FIG. 2) on its upper surface which is aligned with the button 38. The membrane 44 covers an opening in the handle forward section and is sealed with respect to the opening to prevent the passage of fluid between the handle forward section 22 and the membrane 44. The membrane 44 can, for example, be co-molded with the connector 22 or otherwise bonded to the handle forward section 22 to form this seal. The membrane 44 is shown to be partially sunken to form a thumb receiving depression 44a. By pressing on the membrane 44, the button 38 will be moved radially to activate or deactivate the driver.

A speed selector assembly 50 is received in an opening on the opposite side of the handle forward section 22 from the membrane 44. The speed selector 50 is operatively connected to the speed switch 42 to control the position of the speed switch 42. The speed selector assembly 50 includes a cover 52 sized to be received in and to seal with a second opening in the handle forward section 22. The cover 52 forms a recess 53 (FIG. 1) having an elongate slot formed therein. A switch block 54 is received in the cover recess 53 and is sized such that the outer surface of the block will be flush with the outer surface of the handle forward section 22. The block 54 includes a rib 56 which extends through the slot in the switch cover 52. A hole 57 extends through the block 54 behind the rib 56; and a push button 58 extends through the hole.

On its inner surface, the switch cover 52 includes a pair of opposed guides 59 which are on opposite sides of, and extend generally parallel to, the cover slot. A switch block fixture 60 is positioned between the switch cover guides 59 to be movable axially between the guides 59. The switch block fixture 60 is operatively connected to the switch block 54, and is moved axially by movement of the switch block 54. A pole 62 extends from the inner surface of the switch block fixture 60. The pole 62 can, for example, be formed from a screw which is threaddedly connected to the switch block fixture. The pole 62 is sized to engage the sliding switch 42.

As can be appreciated, when the operator moves the switch block 54, the movement of the switch block will be transferred to the sliding switch 42. The engagement of the sliding switch 42 and the control board 40 is one such that as the switch is moved relative to the control board 40, the electrical output from the control board is adjusted. The push button 58 maintains the switch block 54, and hence, the sliding switch 42, in a desired position relative to the control board. In the illustrative embodiment shown, the switch is configured to provide for three discrete output levels. Although a slide is disclosed to enable the electrical output from the control board to be changed, other mechanisms can be used as well. For example, a thumb wheel could be used, and the position of the thumb wheel could be determined using any desired means to determine the position of the wheel, and hence the desired output from the control board. Alternatively, a button, or a plurality of buttons could be used. If one button is used, each time the button is pressed, the output could change between a plurality of preselected, discrete outputs. If two buttons are used, one button could be an output increasing button and the other could be an output decreasing button. In this case, the output would increase or decrease based upon the amount of time the button is depressed. Further, a plurality of buttons could be used, in which case, each button would represent a discrete output.

A motor mount 64 is received in the forward end of the handle forward section 22. The motor mount 64 includes a body 65 and a base portion 66 at one end of the body 65. A ring or flange 67 separates the body 65 from the base portion 66. An O-ring 68 is received in a groove on the base portion 66. The base portion 64 is sized and shaped to be frictionally received in the forward opened end of the handle forward section 22 with the ring or flange 67 resting on the inner step 22b. The O-ring 68 forms a fluid tight seal between the motor mount base portion 64 and the handle forward section 22 below the step 22b. As can be appreciated, a slight gap will be formed around the motor mount body 64 and the handle forward portion step 22a.

A pair of opposed arms 70 extend forwardly from the forward end of the motor mount 64. The motor mount 64 is received in the handle forward section 22 such that the arms 70 extend beyond the forward end of the handle forward section 22. The arms 70 are flexible and include inwardly extending fingers at the ends thereof. A motor 74 is received in the motor mount 64. The motor mount arms 70 are sized such that the arm fingers extend over the end of the motor 74. The motor 74 will therefore be securely held in the motor mount 64 by the arms 70. The flexibility of the arms 70 facilitates insertion of the motor 74 between the arms.

The motor 74 is an electric motor having an output shaft 76. As is known, the driver 10 includes wires which electrically connect the battery 28, the control board 40, the on/off button 38, the speed switch 42 and the motor 74. Thus, the motor can be activated by pressing of the button 38 and the motor speed will be controlled by movement of the speed switch 42 by means of the switch block 54. The speed switch can have discreet settings such that the motor is operated at a determined number of set speeds (i.e., low, medium and high). Alternatively, the speed switch can be continuously variable so that the motor can be operated at any desired speed along a continuum of speeds from a high speed to a low speed.

An ellipse block 80 is fixed to the motor output shaft 76 to be rotated thereby. The ellipse block 80 comprises a base 82 having a bore in the bottom thereof sized to fit over the motor output shaft 76. The ellipse block base 82 can be secured to the output shaft 76 in any desired manner to ensure that the ellipse block will be rotated by rotation of the output shaft 76. For example, a set screw can be used or the bore in the ellipse block base 82 can be keyed to the shaft 76. The ellipse block 80 includes a body 84 at the forward of the base 82. A hole 86 is formed in the end surface of the body 84. As seen, the hole 86 is offset from the axis of the motor shaft 76. Hence, the hole 86 will move in an orbital or eccentric pattern as the ellipse block is rotated by the motor 74.

The driver neck 16 fits over the motor 74 and motor mount 60. The driver neck 16 includes an axially extending generally circumferential lip 16a which is received in the gap between the motor mount 64 and the handle forward section 22. The forward end of the neck 16 is provided with a pair of opposed arms 90 defining a slot or gap 91 therebetween. The arms 90 define a tip to the neck 16. As seen, the arms have axially sloped and circumferentially curved outer surfaces, such that the neck tip is generally in the shape of a blunt or flattened cone. An opening 92 is formed in each of the arms 90. The openings 92 are aligned with each other and extend generally perpendicularly to the gap between the arms. At the base of the arms 90, the neck 16 is stepped, as at 16b,c; and each step 16b,c defines a shoulder.

A driven member 100 is mounted in the neck tip. The member 100 comprises a mounting portion 102 in the form of a ring. The mounting portion is sized to fit in the gap 91 between the neck arms 90. A bushing 104 is received within the mounting portion 102, and a pin, axle or rod 106 extends through the bushing and into the opposed openings 92 in the arms. Hence, the pin 106 defines an axis about which the member 100 can pivot. Importantly, the mounting portion 102 is narrower than the gap between the arms 90, such that the portion 102 (and the member 100) can move freely relative to the arms 90.

Figure 5:
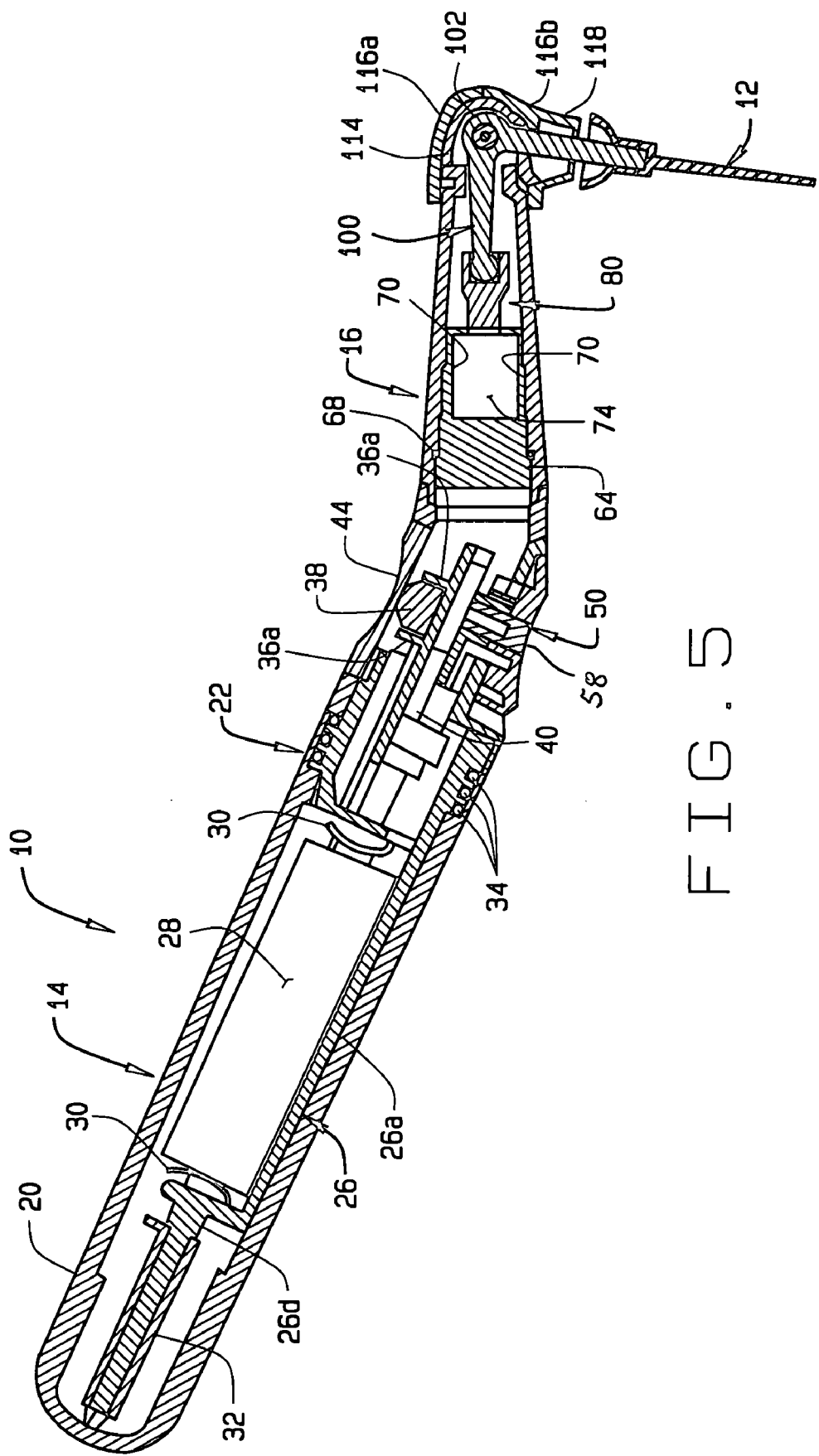
FIG. 5 is a cross-sectional view of the driver with an activator mounted thereto.
Figure 8:
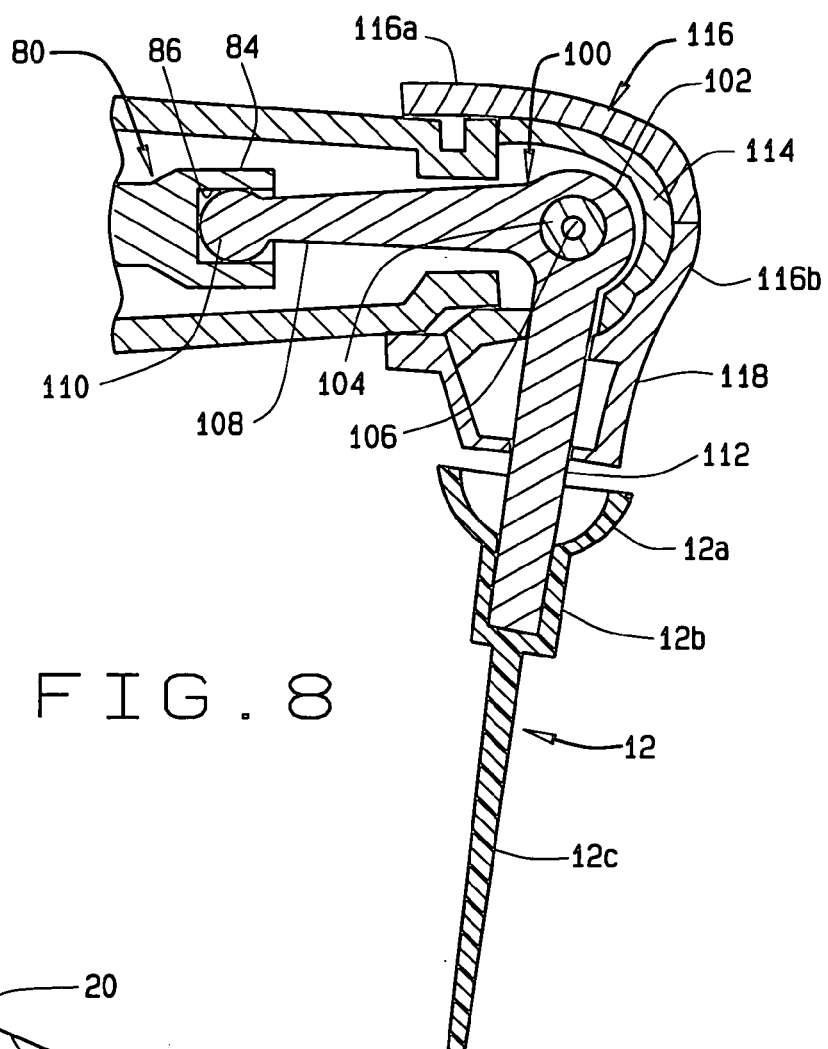
FIG. 8 is an enlarged cross-sectional view of the forward end of the driver showing the mounting of a driven member in the driver and the connection of an activator to the driven member.
Figure 9:
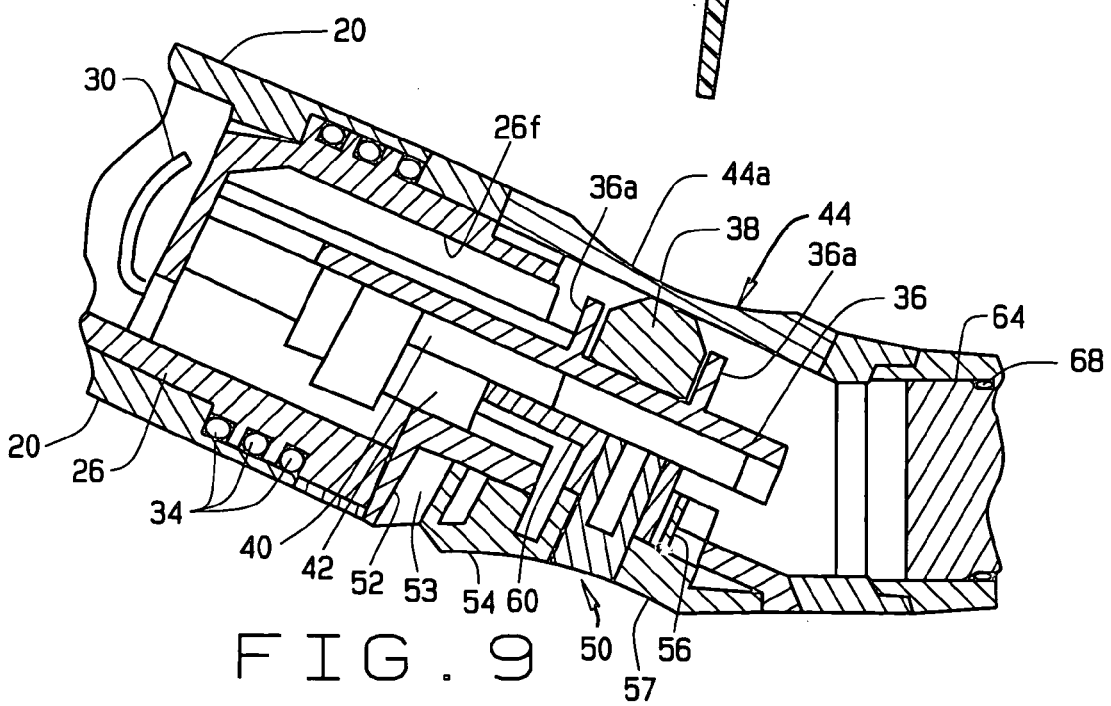
FIG. 9 is an enlarged cross-sectional view showing the activation and control switches of the driver.

A connecting arm 108 extends downwardly from the mounting portion 102 into the neck 16. A connection member or ball 110 is formed at the free end of the connecting arm 108. The connecting arm 108 is sized such that the ball 110 is received in the hole 86 of the ellipse block 84. As seen in FIGS. 4, 5 and 8. the connecting arm 108 has an outer surface between the mounting portion and the ball that is substantially straight and uninterrupted. A mounting arm 112 extends from the mounting portion 102 and forms an angle with the connecting arm of between about 80° and about 90°. The angle can be, for example, about 82°. The mounting arm 112 includes a first part 112a which is generally cylindrical and a second part 112b which has flattened sides.

Figure 6:
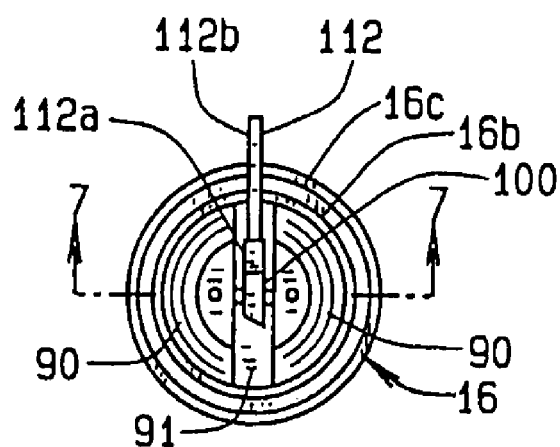
FIG. 6 is an end elevational view of the driver with the cover removed showing the mounting of a vibrational member to the tip of the driver.
Figure 7:
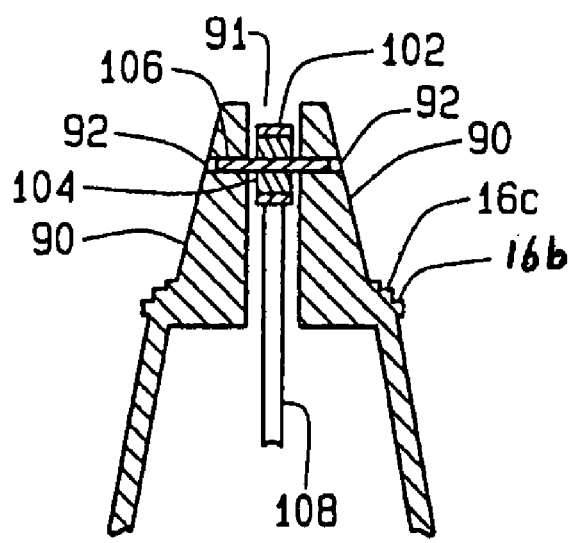
FIG. 7 is a cross-sectional view taken along line 7-7 of FIG. 6.

As seen in FIGS. 6 and 8, the mounting arm 112 has a length such that it extends beyond the outer surfaces of the neck 16.

A cover 114 is received over the tip of the neck 16. The cover 114 is made from a flexible material, such as silicon rubber. The cover includes a body 114a and a nose 114b. The cover body 114a is sized and shaped to snugly fit over and about the arms 90 of the sleeve 16. The nose 114b is positioned on the cover body 114a to be aligned with the gap between the arms 90 and to be in the plane of the arm holes 92, such that the mounting arm 112 of the driven member 100 will extend through the nose 114b. The nose 114b is cylindrical in shape, and is sized to fit around the first part 112a of the driven member mounting arm 112. The cover 114 is sized at its bottom end to form a seal with the neck 16, at the step 16c.

The driver 10 further includes a cap 116 which encases the cover 114. The cap is a two piece cap and comprises a back portion 116a and a front portion 116b. The front and back portions of the cap snap together. A nose 118 extends from the cap front portion 116b. The driven member mounting arm 112 extends through the cap nose 118 so that an activator can be mounted on the mounting arm 112.

As shown in the drawings, and as described above, and as described our co-pending application Ser. No. 11/104,678, which is incorporated herein by reference, the activator 12 is includes guard 12a, connection block 12b, and activating tip 12c. The cover nose 118 and the activator guard 12a are respectively sized and shaped such that the guard 12a covers the front of the cover nose 118. While the guard 12a may not form a seal with the nose, the size and shape of the guard relative to the cover nose will help prevent aerosoled, splattered, or sprayed fluids from entering the tip of the driver. The activator connecting block 12b defines a pocket or cavity which is sized and shaped to be snuggly received over the shaped end 112b of the driven member mounting arm 112. The activator 12 is made from a flexible, non-metallic, non-cutting material, and can be made from plastic, nylon, or an aromatic polyamide (such as Kevlar®). The flexibility of the activator (and of the activator connection block 12b) allows for the connection block 12b to be expanded slightly when the block is mounted onto the driven member mounting arm 112. The mounting arm 112 and the connection block pocket have very similar dimensions. Thus, the activator will be held on the mounting arm by frictional forces. Therefore, tools are not required to connect the activator to, or remove the activator from, the driver 10.

In operation, when the driver 10 is activated by means of the button 44, the motor 74 will rotate the ellipse block 80, causing the ellipse block hole 86 to orbit about the motor shaft 76. The orbital motion of the hole 86 will be transferred to the driven member connecting arm 108 through the connection between the driven member connecting arm 108 and the ellipse block hole 86. Hence, the bottom or baii 110 of the driven member 100 will be driven in a circular or orbital path. The connecting ring 102 is loosely mounted on the bushing 104 and pin 106. Further, the bushing and pin are made of materials which will not significantly dampen the vibratory motion induced into the driven member's connecting arm 108. Hence, the vibratory motion of the connecting arm 108 is transferred to the driven member mounting arm 112. The vibratory motion is then transferred to the activator 12.

As noted in the above noted co-pending application, the activator is made from a very flexible material. Hence, the vibrations that are passed to the activator essentially cause the activator tip 12c to oscillate or vibrate. When the activator tip is placed within a root canal filled with fluid, activation of the driver will cause tip to vibrate within the canal. The vibration of the tip will result in cavitation and acoustic streaming resulting in turbulence of the fluid. The vibrating tip will engage the surfaces of the prepared root canal to facilitate removal of the smear layer within the root canal. Further, the fluid turbulence will reach into the lateral anatomy of the root canal to also facilitate deep lateral cleaning.

The activator tip is made from a non-cutting non-metallic material. Hence, vibration of the tip within the root canal will not damage the root canal—it will not create any ledges or otherwise alter the shape of the already prepared root canal.

The motor 74 operates such that the tip 12 will vibrate at sonic frequencies (i.e., less than 15 KHz). The speed switch can be used to adjust the speed of the motor, and hence the rate at which the tip 12 vibrates. As noted above, the switch in the illustrative embodiment provides for three discrete outputs, which drive the activator of frequencies of 2, 6, and 10 kHz. These speeds can be changed if desired to be different speeds, and, the switch assembly can provide for two, three, four or more discrete speeds. Alternatively, the speed switch can be one which allows for a continuum of speeds from a high speed to a low speed.

In the ultrasonically activated endodontic tips such as are noted above in the background which are used to primarily cut dentin or vibrate against metal objects, the vibrational energy passed into the tip must pass through a bend or curve in the instrument itself. Thus, for the cutting end of the tip to vibrate at a proper speed, the tip must be tightly mounted to the driver. Hence, such cutting tips require that the tip be threaded onto the tool and that wrenches be used to tighten the tip to the driver. However, in the instant application, the vibrational energy does not need to be transmitted about any bends after it has been transferred to the activator 12. Hence, the activator 12 need not be so tightly connected or mounted to the driver's mounting arm 112; and, the activator 12 can be frictionally held by the mounting arm 112, as noted above, and connected to, and disconnected from, the driver without the use of tools. In fact, in the design shown, the activator is frictionally fitted onto the mounting arm 112 as noted above, and hence can easily be slipped on and slipped off of the mounting arm 112.

Although the use of rotating ellipse block is shown as the means for inducing vibrational motion in the driven member 100, other means can be used as well. For example, the end of the connecting arm 108 can be provided with a magnet, and this magnet can be adjacent an electromagnet. The electromagnet can then be alternatively energized and de-energized (or its polarity can be continuously alternated) to thereby induce vibrational motion in the connection member 108. Alternatively, such a magnet at the end of the connecting arm can be surrounded by a plurality of electromagnets which are energized to induce motion in the end of the connection member (much in the same way a motor stator causes a motor rotor to rotate).

As various changes could be made in the above constructions without departing from the scope of the invention, it is intended that all matter contained in the above description or shown in the accompanying drawings shall be interpreted as illustrative and not in a limiting sense. For example, although the driver is shown and described to be cordless, the driver could be made to be a corded driver. Additionally, although the driver is shown and described to be contra-angled, the driver could be a straight. Further, the driver could drive the activator at other speeds than disclosed above, and, hence, the activator could be driven at ultrasonic speeds in addition to sonic speeds. If the activator is to be driven ultrasonically, the vibration inducing means may be changed from that disclosed above to a piezoelectric system or a magnetorestrictive system. These examples are merely illustrative.

The invention claimed is:

1. A driver for vibrationally driving an endodontic activator; said driver comprising:
a body having a handle and a neck; said neck including a pair of spaced apart arms extending from an end of said neck; each said arm including a hole extending through said arm, the holes of said arms being aligned with each other; said body defining a contra-angle, wherein said handle and said neck define an angle of between 15°-30° and wherein when said activator is mounted to said body, said activator and said neck define an angle of between 80°- 85°;
a driven member including a mounting portion, a mounting arm extending from said mounting portion to which an endodontic activator is frictionally removably mountable and a connecting arm extending from said mounting portion; said connecting arm having a connection member at an end remote from said mounting portion; said connecting arm having an outer surface between said connection member and said mounting portion that is substantially straight and uninterrupted; said connecting arm and said mounting arm being spaced from each other about said mounting portion, such that said mounting arm and said connecting arm define an angle of between about 80° and about 90°; said driven member mounting portion being shaped and sized to be received between said neck arms; said driven member mounting portion defining a transverse hole which extends through said mounting portion; said driver including an axle which extends through said driven member mounting portion hole and into said neck arm holes; said axle pivotally mounting said driven member in said body and defining a pivot axis generally normal to an axis of said body about which said driven member can pivot; and
a drive; said drive comprising a rotatable ellipse block having an axis of rotation; said driven member connecting arm being operatively connected to said rotatable ellipse block at a point offset from said axis of rotation of said rotatable ellipse block; whereby, when said ellipse block rotates, an end of said driven member connecting arm orbits about said axis of rotation, and the pivotal mounting portion of said driven member in said body converts said orbital motion of said connecting arm to oscillatory motion in said driven member mounting arm.

2. The driver of claim 1 wherein said ellipse block comprises a pocket on an end surface thereof; said ellipse block pocket being off-set from the axis of rotation of said ellipse block, such that when said ellipse block is rotated, said pocket moves in an orbital pattern; said connection member of driven member connecting arm being received in the ellipse block pocket.

3. The drive of claim 2 wherein said ellipse block is operatively connected to an output shaft of an electric motor, said motor rotating said ellipse block when activated.

4. The driver of claim 3 wherein said motor and rotatable block induce vibrations in said activator at sonic frequencies.

5. The driver of claim 1 wherein said neck arms define a gap therebetween; said driven member mounting portion having a width less than the width of said gap such that said driven member mounting portion is mounted in said gap to move freely relative to said arms.

6. The driver of claim 1 comprising a bushing mounted in said mounting portion hole; said axle extending through said bushing.

7. The driver of claim 1 wherein including a switch operable to change the oscillatory speed of the driven member between at least two speeds.

8. The driver of claim 7 wherein the switch is operable to change the oscillatory speed of the driven member along a continuum of speeds between a high speed to a low speed.

9. The driver of claim 1 wherein the driver is cordless; said body carrying a power source.

10. The driver of claim 9 wherein the power source is rechargeable.

11. The driver of claim 1 wherein said activator is frictionally mounted and held to said driven member, such that said activator can be mounted to, and removed from, said driven member without the use of tools.

12. The driver of claim 11 wherein said activator comprises a connection block defining a pocket; said driven member mounting portion being sized relative to said activator connection block pocket such that said driven member mounting portion is substantially the same size as said pocket, whereby said connection block pocket expands slightly when said activator is mounted to said driven member mounting portion.

13. In combination, an endodontic activator and a driver to which said endodontic activator is removably connected and which vibrationally drives said activator; said driver comprising:

a body having a handle, a neck, and a cover for said neck; said neck including a pair of spaced apart arms extending from an end of said neck; each said arm including a hole extending through said arm, the holes of said arms being aligned with each other; said cover enclosing said neck arms and comprising an opening at an end; said body defining a contra-angle wherein said handle and said neck define an angle of between 15°-30° and wherein when said activator is mounted to said body, said activator and said neck define as an angle of between 80°-85°;

a driven member comprising a mounting portion, a connecting arm extending from said mounting portion, and a mounting arm which extends from said mounting portion and has a length sufficient such that a portion of said mounting arm extends through said cover opening; said connecting arm having a connection member at an end remote from said mounting portion said connecting arm having a substantially straight and uninterrupted side surface between said connection member and said mounting portion; said mounting arm and said connecting arm being spaced from each other about said mounting portion such that said mounting arm and said connecting arm define an angle of between about 80° and about 90°; said driven member mounting portion being shaped and sized to be received between said neck arms; said driven member mounting portion defining a transverse hole which extends through said mounting portion; said driver including an axle which extends through said driven member mounting portion hole and into said neck arm holes; said axle pivotally mounting said driven member in said body and defining a pivot axis generally normal to an axis of said body about which said driven member can pivot; and a drive; said drive comprising a rotatable block having an axis of rotation; said connection member of said driven member connecting arm being operatively connected to said rotatable ellipse block at a point offset from said axis of rotation of said rotatable ellipse block; whereby, when said ellipse block rotates, said connection member of said driven member connecting arm orbits about said axis of rotation, and the pivotal mount of said driven member in said body converts said orbital motion of said connecting arm to oscillatory motion in said driven member mounting arm;

said activator comprising:

a mounting block defining a pocket; said pocket being shaped complimentarily to an end of said driven member mounting arm and sized to be frictionally and removably received on said driven member mounting arm; and an activating tip extending from said mounting block.

* * * * *